(12) United States Patent
Dong et al.

(10) Patent No.: US 11,321,561 B2
(45) Date of Patent: May 3, 2022

(54) ELECTROCARDIOGRAM WAVEFORM SIGNAL PROCESSING METHOD AND APPARATUS

(71) Applicant: Huawei Technologies Co., Ltd., Shenzhen (CN)

(72) Inventors: Chen Dong, Beijing (CN); Jie Zhang, Shenzhen (CN); Chao Lv, Shenzhen (CN); Yixin Chen, Beijing (CN); Peida Xu, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 191 days.

(21) Appl. No.: 16/494,573

(22) PCT Filed: Jul. 29, 2017

(86) PCT No.: PCT/CN2017/095073
§ 371 (c)(1),
(2) Date: Sep. 16, 2019

(87) PCT Pub. No.: WO2018/166136
PCT Pub. Date: Sep. 20, 2018

(65) Prior Publication Data
US 2020/0089948 A1    Mar. 19, 2020

(30) Foreign Application Priority Data
Mar. 14, 2017 (CN) .......................... 201710151454.2

(51) Int. Cl.
G06K 9/00    (2006.01)
A61B 5/366    (2021.01)

(52) U.S. Cl.
CPC .......... G06K 9/00503 (2013.01); A61B 5/366 (2021.01); G06K 9/00523 (2013.01); G06K 9/00536 (2013.01)

(58) Field of Classification Search
CPC .......... G06K 9/00503; G06K 9/00536; G06K 9/00523; A61B 5/35; A61B 5/366
See application file for complete search history.

(56) References Cited

U.S. PATENT DOCUMENTS

5,271,411 A * 12/1993 Ripley ................... A61B 5/366
                                                                    600/515
5,301,677 A *  4/1994 Hsung ................... A61B 5/364
                                                                    600/518
(Continued)

FOREIGN PATENT DOCUMENTS

CN    101600390 A    12/2009
CN    103020472 A     4/2013
(Continued)

OTHER PUBLICATIONS

T. Syeda-Mahmood, D. Beymer and F. Wang, "Shape-based Matching of ECG Recordings," 2007 29th Annual International Conference of the IEEE Engineering in Medicine and Biology Society, 2007, pp. 2012-2018, doi: 10.1109/IEMBS.2007.4352714. (Year: 2007).*

(Continued)

*Primary Examiner* — Michael Robert Cammarata
(74) *Attorney, Agent, or Firm* — Conley Rose, P.C.

(57) ABSTRACT

An electrocardiogram waveform signal method includes obtaining a filtered waveform signal, marking the waveform signal as K signal line segments based on monotonicity, extracting line segment data of each signal line segment, and determining a line segment matching template of the waveform signal based on the line segment data of each signal line segment. The extracting of the line segment includes extracting a line segment length Xi and a line segment width Yi of each signal line segment i of the K signal line segments, performing difference extension on the line segment length Xi and the line segment width Yi based on a (Continued)

preset length and a preset width, respectively, to obtain a normalized signal line segment j, and extracting fourth line segment data of the normalized signal line segment j.

20 Claims, 8 Drawing Sheets

(56) References Cited

U.S. PATENT DOCUMENTS

| | | | | |
|---|---|---|---|---|
| 6,564,091 | B2* | 5/2003 | Shekhar | A61B 5/349 600/516 |
| 6,684,100 | B1* | 1/2004 | Sweeney | A61B 5/7264 600/517 |
| 2003/0181818 | A1* | 9/2003 | Kim | A61B 5/35 600/509 |
| 2006/0116595 | A1* | 6/2006 | Palreddy | A61B 5/35 600/516 |
| 2006/0116725 | A1* | 6/2006 | Paireddy | A61N 1/3956 607/5 |
| 2007/0203418 | A1* | 8/2007 | Starc | A61B 5/35 600/509 |
| 2009/0048528 | A1* | 2/2009 | Hopenfeld | A61B 5/366 600/516 |
| 2009/0240300 | A1* | 9/2009 | Lian | A61B 5/7264 607/14 |
| 2010/0069767 | A1* | 3/2010 | Hardahl | A61B 5/349 600/509 |
| 2014/0081162 | A1* | 3/2014 | Snell | A61B 5/366 600/516 |
| 2016/0135706 | A1* | 5/2016 | Sullivan | A61N 1/37211 600/301 |
| 2017/0368360 | A1* | 12/2017 | Hahn | A61N 1/36514 |
| 2018/0008831 | A1* | 1/2018 | An | A61N 1/3756 |
| 2018/0056079 | A1* | 3/2018 | Hahn | A61B 5/352 |

FOREIGN PATENT DOCUMENTS

| | | |
|---|---|---|
| CN | 103190901 A | 7/2013 |
| CN | 103488751 A | 1/2014 |
| CN | 102379694 B | 7/2014 |
| CN | 103961089 A | 8/2014 |
| CN | 104102915 A | 10/2014 |
| CN | 104161510 A | 11/2014 |
| CN | 104523266 A | 4/2015 |
| CN | 104706349 A | 6/2015 |
| CN | 104834921 A | 8/2015 |
| CN | 105125206 A | 12/2015 |
| CN | 105590011 A | 5/2016 |
| CN | 106093467 A | 11/2016 |
| CN | 106137184 A | 11/2016 |
| CN | 106473750 A | 3/2017 |
| FR | 2973998 A1 | 10/2012 |

OTHER PUBLICATIONS

K. A. Salam and G. Srilakshmi, "An algorithm for ECG analysis of arrhythmia detection," 2015 IEEE International Conference on Electrical, Computer and Communication Technologies (ICECCT), 2015, pp. 1-6, doi: 10.1109/ICECCT.2015.7226130. (Year: 2015 ).*

Mazomenos EB, Chen T, Acharyya A, Bhattacharya A, Rosengarten J, Maharatna K. 2012 A time-domain morphology and gradient based algorithm for ECG feature extraction. In 2012 IEEE Int. Conf. on. Ind. Technol. (ICIT), 117-122. (doi: 10.1109/ICIT.2012. 6209924) (Year: 2012).*

Yahya, M. Benaissa and S. Clark, "Application of Adaptive Filtering and Linear Regression for Determining T-Wave Limits in Neonatal ECG," 2007 5th Student Conference on Research and Development, 2007, pp. 1-6, doi: 10.1109/SCORED.2007.4451434. (Year: 2007).*

M. Galeano, A. Calisto, A. Bramanti, S. Serrano, G. Campobello and B. Azzerboni, "R-point detection for noise affected ECG recording through signal segmentation," 2010 Annual International Conference of the IEEE Engineering in Medicine and Biology, 2010, pp. 638-641, doi: 10.1109/IEMBS.2010.5627258. (Year: 2010).*

Machine Translation and Abstract of Chinese Publication No. CN102379694, Jul. 16, 2014, 9 pages.

Machine Translation and Abstract of Chinese Publication No. CN103190901, Jul. 10, 2013, 13 pages.

Machine Translation and Abstract of Chinese Publication No. CN104102915, Oct. 15, 2014, 18 pages.

Machine Translation and Abstract of Chinese Publication No. CN104161510, Nov. 26, 2014, 17 pages.

Machine Translation and Abstract of Chinese Publication No. CN104523266, Apr. 22, 2015, 22 pages.

Machine Translation and Abstract of Chinese Publication No. CN104834921, Aug. 12, 2015, 15 pages.

Machine Translation and Abstract of Chinese Publication No. CN105125206, Dec. 9, 2015, 11 pages.

Machine Translation and Abstract of Chinese Publication No. CN105590011, May 18, 2016, 16 pages.

Machine Translation and Abstract of Chinese Publication No. CN106137184, Nov. 23, 2016, 11 pages.

Machine Translation and Abstract of French Publication No. FR2973998, Oct. 19, 2012, 18 pages.

Pan, J., et al., "A Real-Time QRS Detection Algorithm," IEEE Transactions on Biomedical Engineering, vol. 32, No. 3, Mar. 1985, pp. 230-236.

Martinez, J., "A Wavelet-Based ECG Delineator: Evaluation on Standard Databases," IEEE Transactions on Biomedical Engineering, vol. 51, No. 4, Apr. 2004, pp. 570-581.

Chen, T., "Enhancing The Diagnostic Quality of ECGs in Mobile Environments," Doctoral Thesis, University of Southampton, Apr. 2015, 248 pages.

Hamilton, P., et al., "Quantitative Investigation of QRS Detection Rules Using the MIT/BIH Arrhythmia Database," IEEE Transactions on Biomedical Engineering, vol. BME-33, No. 12, Dec. 1986, pp. 1157-1165.

Foreign Communication From A Counterpart Application, PCT Application No. PCT/CN2017/095073, English Translation of International Search Report dated Dec. 6, 2017, 2 pages.

Foreign Communication From A Counterpart Application, PCT Application No. PCT/CN2017/095073, English Translation of Written Opinion dated Dec. 6, 2017, 4 pages.

Akhbari, M., et al., "ECG segmentation and fiducial point extraction using multi hidden Markov model," Preprint submitted to Journal of Computers in Biology and Medicine, Sep. 8, 2016, 27 pages.

Chen, L., "Research On Representation and Similarity Measurement of ECG Time Series", Dissertation for the Master Degree in Engineering, Dec. 2015, 61 pages. With an English Abstract.

* cited by examiner

ELECTROCARDIOGRAM WAVEFORM SIGNAL PROCESSING METHOD AND APPARATUS

CROSS-REFERENCE TO RELATED APPLICATIONS

This application is national stage of International Application No. PCT/CN2017/095073, filed on Jul. 29, 2017, which claims priority to Chinese Patent Application No. 201710151454.2, filed on Mar. 14, 2017. Both of the aforementioned applications are hereby incorporated by reference in their entireties.

TECHNICAL FIELD

This application relates to the field of signal processing, and in particular, to a waveform signal processing method and apparatus.

BACKGROUND

Currently, as wearable devices become increasingly popular, an implementation in which a sensor is disposed in a wearable device to detect sign signals of a user such as an electrocardiogram signal, a blood flow signal, and a motion signal also emerges. The electrocardiogram signal, a photoplethysmogram signal, or the motion signal that is detected by the sensor in the wearable device is usually a waveform signal having features such as periodicity and continuity. Therefore, a function such as sensing a health status of the user or detecting a step count period can be implemented by monitoring the waveform signal.

However, the waveform signal detected by the sensor of the wearable device may be easily affected by a factor such as a manner of wearing the wearable device or an action of the user, and relatively loud noise included in the waveform signal causes an abnormal phenomenon such as an unstable waveform of the waveform signal or an unstable signal period. Consequently, quality of the waveform signal is poor and reliability of the waveform signal is low.

SUMMARY

Embodiments of this application provide a waveform signal processing method and apparatus, to extract a feature of a signal line segment of a waveform signal, improve efficiency of identifying a period of the waveform signal, and improve applicability of the waveform signal.

A first aspect provides a waveform signal processing method. In the method, processing such as cleaning and filtering may first be performed on an original waveform signal, to obtain a filtered waveform signal. Further, the waveform signal may be marked as K signal line segments based on monotonicity, where K is an integer greater than or equal to 2, and line segment data of each signal line segment is extracted. In this embodiment of this application, the waveform signal is segmented, and feature data of each line segment is extracted through segmentation, so that signal processing accuracy of the waveform signal can be improved and feature identification accuracy of the waveform signal can be improved. In the method, a line segment matching template of the waveform signal may further be determined based on the line segment data of each signal line segment, where the line segment matching template includes M consecutive signal line segments, and M is an integer less than K; each of the K signal line segments obtained by dividing the waveform signal is matched with the M signal line segments included in the line segment matching template, and a target wave group of the waveform signal is determined based on a matching result of each signal line segment; and periodic signal data of the waveform signal is determined based on line segment data of the target wave group.

In this embodiment of this application, the line segment matching template used to identify a period of the waveform signal may be determined based on the extracted feature data of each line segment. The line segment matching template is closely related to the waveform signal. In this embodiment of this application, a target wave group in a single period of the waveform signal may first be determined by using the line segment matching template, and then a period of the waveform signal is identified by using the target wave group, so that period identification accuracy of the waveform signal is higher, signal processing quality of the waveform signal is improved, and applicability is better.

Optionally, in this embodiment of this application, the waveform signal may be divided into monotonically upward signal line segments or monotonically downward signal line segments based on the monotonicity, and the signal line segments are sequentially numbered based on time continuity to obtain line segments having sequential numbers. In this embodiment of this application, the waveform signal may be divided into a plurality of signal line segments base on monotonicity of the line segments, and the monotonicity of each signal line segment is unique, so that the signal line segments may be sequentially numbered based on the time continuity, to better extract feature data of each signal line segment. Integrating the feature data of each signal line segment based on the time continuity can better determine the line segment matching template, improve efficiency of identifying a target wave group of the waveform signal, improve period identification accuracy of the waveform signal, so that applicability is better.

Optionally, in this embodiment of this application, a line segment length Xi and a line segment width Vi of the signal line segment i may be extracted, and difference extension is performed on Xi and Yi based on a preset length and a preset width respectively to obtain a normalized signal line segment j; and line segment data of the signal line segment j is extracted, where the line segment data of the signal line segment j includes at least one of: a middle point position of the line segment, a curvature of a start point position of the line segment, a curvature of an end point position of the line segment, a ray tangent point at which the start point position of the line segment is tangent to the line segment, and a ray tangent point at which the end point position of the line segment is tangent to the line segment. In this embodiment of this application, an individual feature of each signal line segment may be extracted, and the feature of each signal line segment is extracted after each signal line segment is normalized, so that the feature of each signal line segment can be better identified, to process the waveform signal based on the feature of each signal line segment to further improve processing quality of the waveform signal.

Optionally, in this embodiment of this application, the signal line segment j may further be derived or differentiated to obtain a derivative curve of the signal line segment j, and line segment data of the derivative curve may be extracted. The line segment data of the derivative curve includes at least one of: a quantity of inflection points, positions of the inflection points, a middle point position between neighboring inflection points, and a position of an inflection point at which a crest value is the largest. In this embodiment of this application, each signal line segment obtained by dividing the waveform signal may be derived or differentiated, to extract line segment data of a derived or differentiated derivative curve. A feature of each signal line segment obtained by dividing the waveform signal may further be identified, so that extraction accuracy of the feature data of the line segment of the waveform signal is improved and processing quality of the waveform signal is improved.

Optionally, in this embodiment of this application, M target signal line segments whose line segment data is less than a preset line segment data threshold may be selected from the line segment data of the signal line segments, and the M target signal line segments are combined in a preset line segment combination manner to obtain the line segment matching template of the waveform signal. The M target signal line segments are line segments whose sequence numbers are consecutive. In this embodiment of this application, the line segment matching template of the waveform signal may be obtained based on the line segment data of each signal line segment of the waveform signal, so that the line segment matching template and the waveform signal is more closely associated with each other, and accuracy of identifying the period of the waveform signal by using the line segment matching template can be improved, and applicability is better.

Optionally, in this embodiment of this application, the line segment data of each of the K signal line segments may be matched with the line segment data of each of the M target signal line segments included in the line segment matching template, and N valid signal line segments are determined in the K signal line segments, where N is an integer less than M, and a feature difference between line segment data of the valid signal line segment and line segment data of any target line segment included in the line segment matching template is not less than a preset threshold. If the N valid signal line segments include M valid signal line segments whose sequence numbers are consecutive, and a feature difference between the M valid signal line segments and the M target signal line segments included in the line segment matching template is less than the preset threshold, it is determined that positions of the M valid signal line segments are positions of the target wave group.

In this embodiment of this application, the positions of the target wave group included in the waveform signal may be identified, from each signal line segment included in the waveform signal, based on the line segment matching template of the waveform signal and a preset data error threshold, to further identify a period of the waveform signal based on the positions of the target wave group, so that period identification accuracy of the waveform signal is improved, processing quality of the waveform signal can be improved, and applicability is better.

Optionally, line segment data at the positions of the target wave group includes the line segment data of the M valid signal line segments at the positions of the target wave group and line segment data of J neighboring signal line segments whose sequence numbers are consecutive to the sequence numbers of the M valid signal line segments. In this embodiment of this application, at least one type of the following wave group feature data: a waveform width of a wave group including the M valid signal line segments and the neighboring signal line segments, a waveform amplitude of the wave group, a height of a start point of the wave group or fluctuation of an end point of the wave group may be determined based on the line segment data of the M valid signal line segments and the line segment data of the J neighboring signal line segments. If a feature difference between the wave group feature data and period checking data is less than a preset period threshold, it is determined that the wave group is a period of the waveform signal. The wave group feature data is the periodic signal data of the waveform signal. The period checking data includes at least one of: a waveform width of the period, a waveform amplitude of the period, a waveform height of a start point of the period, and a waveform height of an end point of the period. In this application, the period of the waveform signal may be identified based on information such as the positions of the target wave group of the waveform signal and period checking data of the waveform signal that are obtained through identification, thereby improving period identification convenience and accuracy of the waveform signal.

Optionally, in this embodiment of this application, a plurality of waveform periods included in the waveform signal may be determined based on the periodic signal data of the waveform signal and abnormal period data included in the waveform signal may be deleted. The abnormal period data is line segment data of a wave group that does not include the periodic signal data in the waveform signal. In this embodiment of this application, the abnormal period data in the waveform signal may be deleted, to improve signal quality of the waveform signal and improve applicability of the waveform signal.

Optionally, the waveform signal described in this embodiment of this application may include at least one of: an electrocardiogram ECG, a photopiethysmogram PPG, a pressure gauge signal, a magnetometer signal, and an accelerometer sensor waveform signal. The method provided in this embodiment of this application is applicable to processing of a plurality of types of waveform signals, an operation is flexible, and an application range is wide.

A second aspect provides a waveform signal processing apparatus. The waveform signal processing apparatus may include:

an obtaining unit, configured to obtain a filtered waveform signal;

a segmentation unit, configured to mark the waveform signal obtained by the obtaining unit as K signal line segments based on monotonicity, where K is an integer greater than or equal to 2;

an extraction unit, configured to extract line segment data of each signal line segment obtained by the segmentation unit through processing; and a processing unit, configured to determine a line segment matching template of the waveform signal based on the line segment data of each signal line segment extracted by the extraction unit, where the line segment matching template includes M consecutive signal line segments, and M is an integer less than K, where the processing unit is further configured to: match each of the K signal line segments obtained by the segmentation unit through processing with the M signal line segments included in the line segment matching template, and determine a target wave group of the waveform signal based on a matching result of each signal line segment; and the processing unit is further configured to determine, based on line segment data of the target wave group, periodic signal data of the waveform signal obtained by the obtaining unit.

Optionally, the segmentation unit is configured to:

divide the waveform signal into monotonically upward signal line segments or monotonically downward signal line segments based on the monotonicity, and sequentially number the signal line segments based on time continuity to obtain line segments having sequential numbers.

Optionally, the extraction unit is configured to:

extract a line segment length Xi and a line segment width Yi of the signal line segment and perform difference extension on Xi and Yi based on a preset length and a preset width respectively to obtain a normalized signal line segment j; and extract line segment data of the signal line segment j, where the line segment data of the signal line segment j includes at least one of: a middle point position of the line segment, a curvature of a start point position of the line segment, a curvature of an end point position of the line segment, a ray tangent point at which the start point position of the line segment is tangent to the line segment, and a ray tangent point at Which the end point position of the line segment is tangent to the line segment.

Optionally, the extraction unit is further configured to:

derive or differentiate the signal line segment j to obtain a derivative curve of the signal line segment j, and extract line segment data of the derivative curve, where the line segment data of the derivative curve includes at least one of: a quantity of inflection points, positions of the inflection points, a middle point position between neighboring inflection points, and a position of an inflection point at which a crest value is the largest.

Optionally, the processing unit is configured to:

select M target signal line segments whose line segment data is less than a preset line segment data threshold from the line segment data of the signal line segments, and combine the M target signal line segments in a preset line segment combination manner to obtain the line segment matching template of the waveform signal, where the M target signal line segments are line segments whose sequence numbers are consecutive.

Optionally, the processing unit is configured to:

match the line segment data of each of the K signal line segments with the line segment data of each of the M target signal line segments included in the line segment matching template, and determine N valid signal line segments in the K signal line segments, where N is an integer less than M, and a feature difference between line segment data of the valid signal line segment and line segment data of any target line segment included in the line segment matching template is not less than a preset threshold; and if the N valid signal line segments include M valid signal line segments whose sequence numbers are consecutive, and a feature difference between each of the M valid signal line segments and the M target signal line segments included in the line segment matching template is less than the preset threshold, determine that positions of the M valid signal line segments are positions of a target wave group.

Optionally, line segment data at the positions of the target wave group includes the line segment data of the M valid signal line segments at the positions of the target wave group and line segment data of J neighboring signal line segments whose sequence numbers are consecutive to the sequence numbers of the M valid signal line segments.

The processing unit is configured to:

determine, based on the line segment data of the M valid signal line segments and the line segment data of the J neighboring signal line segments, at least one type of the following wave group feature data: a waveform width of a wave group including the M valid signal line segments and the J neighboring signal line segments, a waveform amplitude of the wave group, a height of a start point of the wave group, or fluctuation of an end point of the wave group; and if a feature difference between the wave group feature data and period checking data is less than a preset period threshold, determine that the wave group is a period of the waveform signal and the wave group feature data of the wave group is the periodic signal data of the waveform signal, where the period checking data includes at least one of: a waveform width of the period, a waveform amplitude of the period, a waveform height of a start point of the period, and a waveform height of an end point of the period.

Optionally, the processing unit is further configured to:

determine, based on the periodic signal data of the waveform signal, a plurality of waveform periods included in the waveform signal, and delete abnormal period data included in the waveform signal, where the abnormal period data is line segment data of a wave group that does not include the periodic signal data in the waveform signal.

Optionally, the waveform signal includes at least one of: an electrocardiogram ECG, a photoplethysmogram PPG, a pressure gauge signal, a magnetometer signal, and an accelerometer sensor waveform signal.

A third aspect provides a terminal device. The terminal device may include a processor, a memory, a transceiver, and a bus system, where the memory, the processor, and the transceiver are connected by using the bus system;

the memory is configured to store a set of program code; and the processor and the transceiver are configured to invoke the program code stored in the memory to perform the method provided in the first aspect.

According to a fourth aspect, an embodiment of this application provides a computer storage medium, configured to store a computer software instruction used by the foregoing terminal device, and the computer software instruction includes a program designed for performing the first aspect.

According to a fifth aspect, an embodiment of this application further provides a chip. The chip is coupled to a transceiver in a terminal device, to perform the technical solution in the first aspect of the embodiments of this application. It should be understood that, "coupling" in this embodiment of this application means that two components are directly or indirectly combined with each other. Such combination may be fixed or movable, and may allow flow of liquid, electricity, an electrical signal, or another type of signal to communicate between the two components.

In the embodiments of this application, individual line segment data of a signal line segment may be extracted from the waveform signal, processing such as derivation may further be performed on the signal line segment and the line segment data of the derivative curve may be extracted, and a line segment matching template that is used for identifying the periodic signal data of the waveform signal is built based on extracted combined feature data of the line segment data. Further, the period of the waveform signal may be identified by using the line segment matching template, and noise is deleted. The line segment matching template provided in the embodiments of this application may be built by using the line segment data of the waveform signal. The line segment matching template may vary due to different feature data of the waveform signal, so that the association between the line segment matching template and the line segment data of the waveform signal can be improved, the period identification accuracy of the waveform signal can be improved, and noise deletion accuracy can be improved, the processing quality of the waveform signal can be improved, and the applicability is good.

BRIEF DESCRIPTION OF DRAWINGS

To describe the technical solutions in the embodiments of this application more clearly, the following briefly describes the accompanying drawings required for the embodiments. Apparently, the accompanying drawings in the following description show merely some embodiments of this application, and a person of ordinary skill in the art may still derive other drawings from these accompanying drawings without creative efforts.

DESCRIPTION OF EMBODIMENTS

The following clearly and completely describes the technical solutions in the embodiments of this application with reference to the accompanying drawings in the embodiments of this application.

During specific implementation, a signal processing method and apparatus provided in the embodiments of this application are applicable to processing of any one-dimensional waveform signal that is periodic. The one-dimensional waveform signal includes but is not limited to an ECG signal collected by an electrocardiogram (electrocardiogram, ECG) sensor, a PPG signal collected by a photoplethysmogram (photoplethysmography, PPG) sensor, a pressure gauge signal (including a barometer signal), waveform signals collected by an angular velocity sensor of a gyroscope and an accelerometer sensor, and the like. This is not limited herein. For ease of description, the ECG signal is used as an example for description in the embodiments of this application.

The embodiments of this application are further applicable to processing of an aperiodic signal, for example, a magnetometer signal, and may be used to identify a line segment combination in the aperiodic signal. The aperiodic signal may be specifically determined based on an actual application scenario. This is not limited herein.

Usually, the one-dimensional waveform signal that is periodic may be a waveform signal repeated periodically, for example, a heart rate signal recorded by the ECG signal. A heartbeat is periodic, and each heartbeat has a corresponding waveform signal. Therefore, a quantity of heartbeats indicates a quantity of heartbeat periods. A waveform signal of each heartbeat period may be recorded by using an ECG sensor or the like, to obtain a one-dimensional waveform signal that is periodic.

Figure 1:
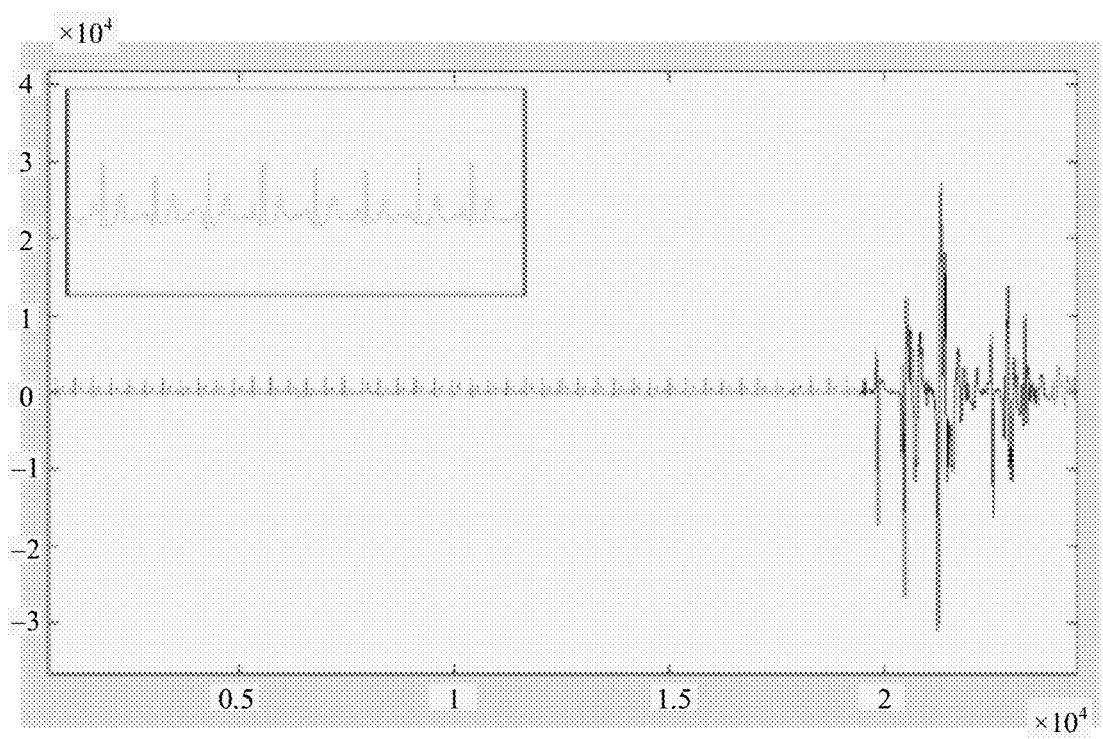
FIG. 1 is a schematic diagram of a waveform signal according to an embodiment of this application.

During specific implementation, a sensor such as the ECG sensor may be specifically a sensor disposed in a terminal device such as a wearable device. Due to an objective factor such as a manner of wearing the wearable device, a manner of fixing the sensor, and an action of a user, a waveform signal detected by the sensor includes relatively loud noise. This causes an abnormal phenomenon such as an unstable waveform of the waveform signal or an unstable signal period. For example, FIG. 1 is a schematic diagram of a waveform signal according to an embodiment of this application. As shown in FIG. 1, the waveform signal is an ECG signal having a time length of one minute and a sampling frequency of 500 hertz (Hz). The waveform signal shown in FIG. 1 is a filtered waveform signal and includes a noise part and a stable signal (a normal signal) part. A waveform in the noise part is unstable, crest heights are different, and a crest in a sharpest part is much higher than other crests. Parts on the left and the right of the noise part are the normal signals. In the parts the waveform signal changes periodically, a waveform shape is similar in each period, the crest height is stable, and a period length is fixed.

The method and apparatus provided in the embodiments of this application may be used to identify a normal signal part (that is, a period of the waveform signal) in the waveform signal, and further delete a signal in the noise part in the waveform signal to obtain a noise-deleted waveform signal, so that signal quality of the waveform signal can be improved. The waveform signal processing method and apparatus provided in the embodiments of this application are described below with reference to FIG. 2 to FIG. 10. During specific implementation, the waveform signal processing method in the embodiments of this application may be performed by a functional module such as a processor in a terminal device such as a wearable device. This may be specifically determined based on a hardware structure of the terminal device such as the wearable device in an actual application scenario and is not limited herein. The terminal device may further include a smartphone, a tablet computer, a personal computer assistant, a portable electrocardiogram detector, an electrocardiogram monitor, and the like. This is not limited herein. For ease of description, the terminal device is used as an example for description in the embodiments of this application.

Figure 2:
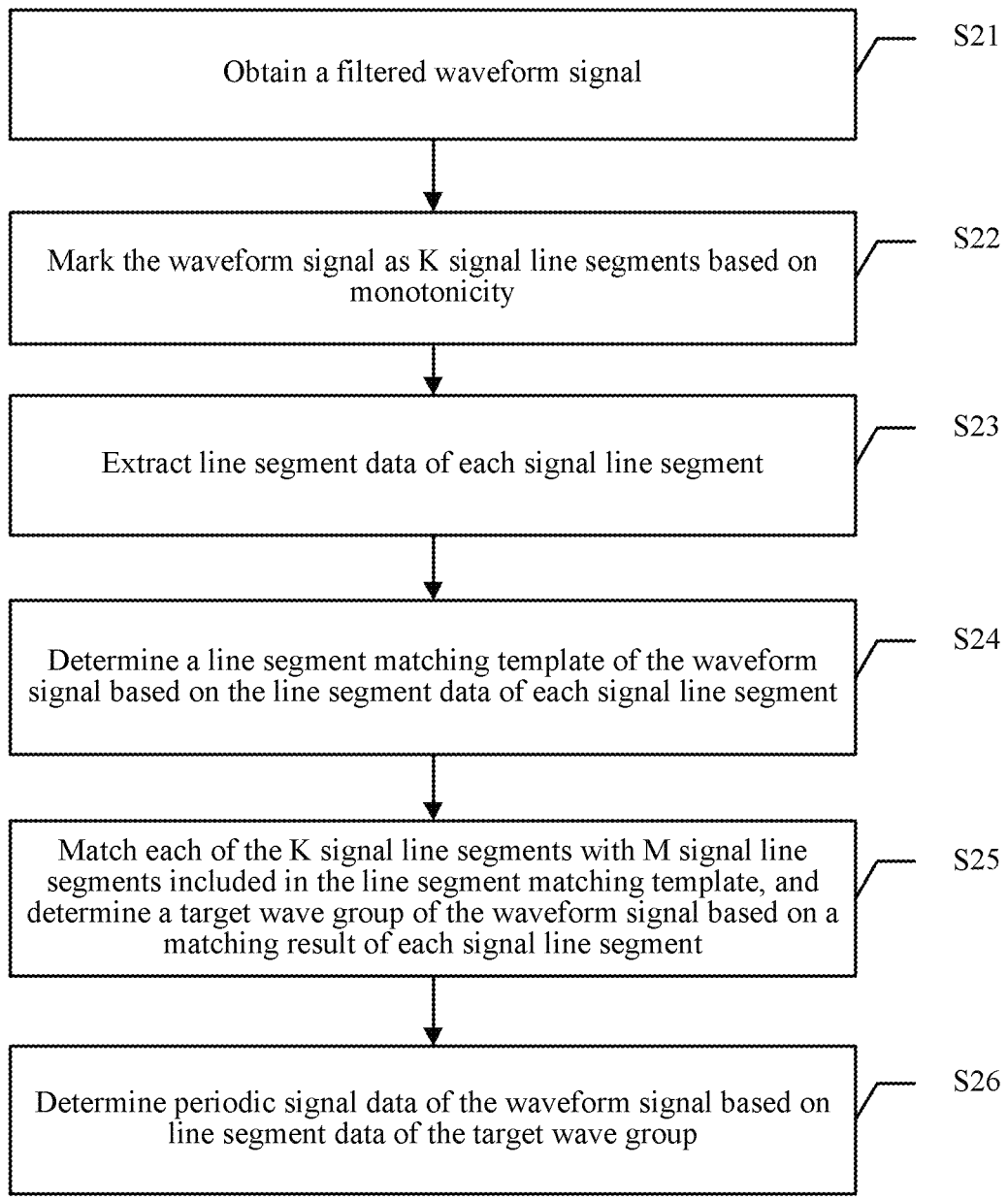
FIG. 2 is a schematic flowchart of a waveform signal processing method according to an embodiment of this application.

FIG. 2 is a schematic flowchart of a waveform signal processing method according to an embodiment of this application. The method provided in this embodiment of this application includes the following steps.

S21. Obtain a filtered waveform signal.

During specific implementation, the terminal device may collect waveform data within a preset time length (for example, one minute) based on a preset collection frequency (for example, 500 Hz), to further perform processing such as cleaning on the collected data to exclude apparently invalid data. The data cleaning may be cleaning of invalid data in the collected data, for example, data having an incomplete waveform, or data having no periodic change, or data that does not confirm to an expected requirement (for example, a non-one-dimensional signal), to obtain data of a waveform signal (for example, an ECG signal) that confirms to the expected requirement. For example, if heartbeats and a heart rate of a person are regular and a heartbeat period is stable, collected data may be cleaned based on heartbeat features of the person to obtain a waveform signal such as an ECG signal that is used to represent a heartbeat. Although including a large noise part, the waveform signal shown in FIG. 1 can be retained through data cleaning because signals on the left and the right of the noise are signals that are periodically stable. If the waveform signal shown in FIG. 1 has no periodically stable signal part but disordered data, the waveform signal may be discarded.

During specific implementation, the terminal device may further filter the data obtained through cleaning, to obtain filtered waveform data. Based on a data processing requirement such as differences of sensors collecting data and different use objectives of the waveform data, the data obtained through cleaning may be filtered by using different filters and corresponding parameters thereof.

Optionally, for the operations such as the waveform signal cleaning and filtering, refer to more existing manners for cleaning and filtering waveform signal data. Specifically, the data cleaning or filtering manners may be determined based on an actual application scenario. This is not limited herein.

S22. Mark the waveform signal as K signal line segments based on monotonicity.

Figure 3:
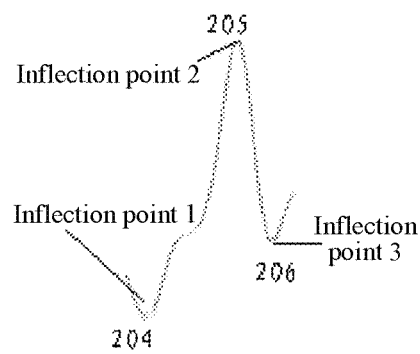
FIG. 3 is another schematic diagram of a waveform signal according to an embodiment of this application.

In some feasible implementations, after the terminal device performs processing such as cleaning and filtering on the collected data, segmentation processing may be performed on a filtered waveform signal. The operation of performing segmentation processing on the waveform signal is not segmenting the waveform signal into line segments, but marking the waveform signal as a plurality of signal line segments based on monotonicity. Specifically, the waveform signal may be marked as K signal line segments based on monotonicity of monotonically upward and monotonically downward, where K is an integer greater than or equal to 2. Each signal line segment has unique monotonicity. Further, all of the K signal line segments may be sequentially numbered based on time continuity, to obtain a line segment carrying a sequence number. FIG. 3 is another schematic diagram of a waveform signal according to an embodiment of this application. In a segment of waveform signal shown in FIG. 3, a horizontal coordinate is waveform generation time and a vertical coordinate is waveform amplitude. The segment of waveform signal may include inflection points 1, 2, and 3, and each inflection point is a monotonicity variation node of a line segment. For example, monotonicity of a line segment on the left of the inflection point 1 is monotonically downward, monotonicity of a line segment on the right of the inflection point 1 is monotonically downward, and therefore the line segment on the left of the inflection point 1 and the line segment on the right of the inflection point 1 may be respectively marked as different signal line segments. The monotonicity of the signal line segment on the left of the inflection point 1 is monotonically downward, and generation time of the signal line segment is earlier than that of the line segment on the right of the inflection point 1. Therefore, the signal line segment may be marked as 204. A signal line segment between the inflection point 1 and the inflection point 2 is monotonically upward, and generation time of the signal line segment is after the inflection point 1. Therefore, the signal line segment between the inflection point 1 and the inflection point 2 may be marked as 205 based on time continuity. Similarly, a signal line segment between the inflection point 2 and the inflection point 3 is monotonically downward, and therefore the signal line segment may be marked as 206. For more signal line segments that are not shown in FIG. 3, signal line segments whose generation time is earlier than that of the signal line segment 204 may be marked as signal line segments 203, 202, 201, . . . , 1, 0, and the like, and signal line segments whose generation time is later than that of the signal line segment 206 may be marked as signal line segments 207, 208, 209, and the like. This is not limited herein.

Optionally, the waveform signal is a wave-shaped curve. Therefore, in the waveform signal, there is certainly a monotonically downward line segment connected to a monotonically upward line segment and then connected to a monotonically downward line segment. Connection points of the line segments are inflection points. Line segments that are monotonically upward and downward are alternately arranged in the waveform signal, and a connection point of the line segment j is a trough or a crest of the waveform signal. The trough and the crest are alternately connected. The terminal device may mark, based on a variation rule of the trough and the crest, a signal line segment having unique monotonicity between any trough (or crest) and a neighboring crest (or trough) thereof as a signal line segment. For example, the inflection point 1 may be a trough of the waveform signal, the inflection point 2 is a crest of the waveform signal, and the inflection point 3 is another trough of the waveform signal. The terminal device may mark a monotonically upward line segment between a trough corresponding to the inflection point and a neighboring crest (the inflection point 2) of the trough as a signal line segment.

Optionally, the terminal device may mark, based on more segmentation and marking manner, a segment of collected waveform signal as a plurality of signal line segments having unique monotonicity. This may be specifically determined base on an actual application scenario and is not limited herein.

S23. Extract line segment data of each signal line segment.

Figure 4:
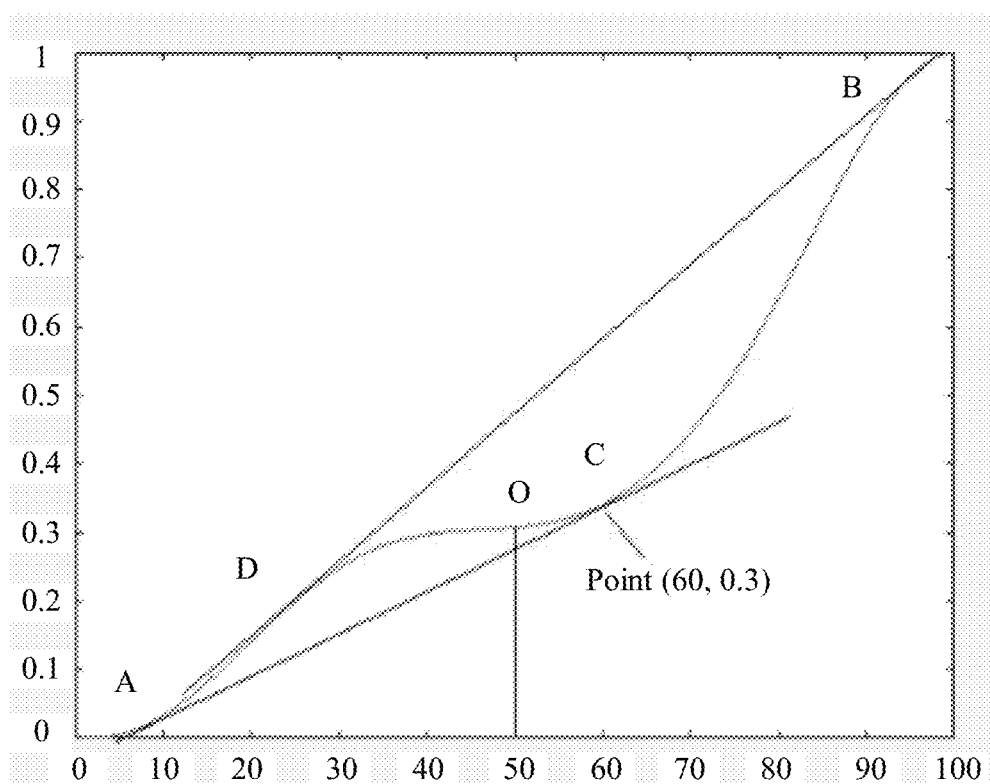
FIG. 4 is another schematic diagram of a waveform signal according to an embodiment of this application.

In some feasible implementations, after marking the waveform signal as the plurality of signal line segments, the terminal device may extract line segment data of each signal line segment. Any signal line segment i is used as an example below to describe a manner of extracting the line segment data of the signal line segment. Specifically, the terminal device may extract a line segment length Xi and a line segment width Yi of the signal line segment i, and separately performs difference extension on Xi and Yi based on a preset length and a preset width respectively to obtain a normalized signal line segment (which may be marked as a signal line segment j). Further, line segment data of the signal line segment j may be obtained. The line segment data of the signal line segment may include but is not limited to: a middle point position of a line segment, a start point position and/or an end point position of the line segment, a curvature of the start point position of the line segment, a curvature of the end point position of the line segment, a ray tangent point at which the start point position of the line segment is tangent to the line segment, a ray tangent point at which the end point position of the signal is tangent to the line segment, and the like. The line segment width may be a time length between the start point and the end point of the line segment. The line segment length may be a variation amplitude between the start point and the end point of the line segment. The position of the middle point of the line segment is a point that is in a waveform signal line segment and corresponding to the middle point of the width of the line segment. For example, FIG. 4 is another schematic diagram of a waveform signal according to an embodiment of this application. The terminal device may perform difference extension on the line segment length Xi and the line segment width Yi of the signal line segment i to a preset size of 1*100, and may then extract line segment data of the signal line segment after the difference extension. The extracted line segment data may include a coordinate position of a middle point O of a line segment, coordinate positions of a start point A of the line segment and an end point B of the line segment, a curvature of the start point A of the line segment, a curvature of the end point B of the line segment, a coordinate position of a ray tangent point C at which the start point A of the line segment is tangent to the line segment, a coordinate position of a ray tangent point D at which the end point B of the line segment is tangent to the line segment, and the like.

Figure 5:
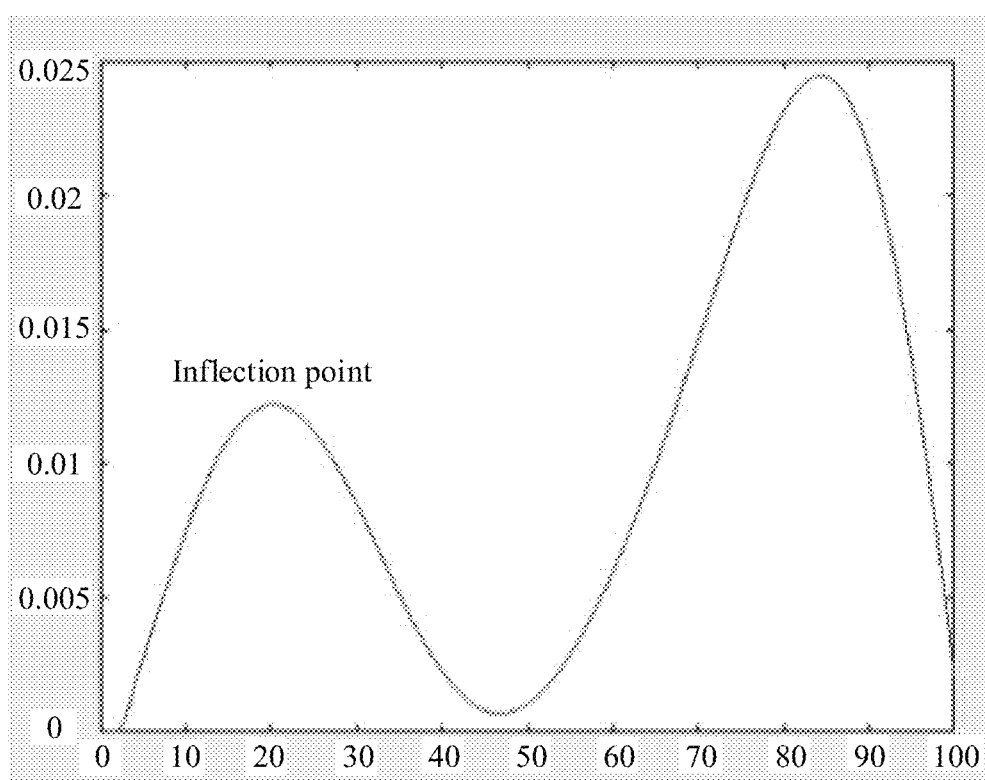
FIG. 5 is a schematic diagram of a derivative curve of a signal line segment according to an embodiment of this application.

Further, the terminal device may further perform derivation on the signal line segment j to obtain a derivative curve of the signal line segment j, and extracts line segment data of the derivative curve. The line segment data of the derivative curve includes data such as a quantity of inflection points, positions of the inflection points, a middle point position between neighboring inflection points, and a position of an inflection point at which a crest value is the largest. This is not limited herein. FIG. 5 is a schematic diagram of a derivative curve of a signal line segment according to an embodiment of this application. The derivative curve shown in FIG. 5 is a schematic diagram of a derivative curve of the signal line segment shown in FIG. 4. Because the signal line segment shown in FIG. 4 is a curve, what is obtained after derivation is performed on the curve is still a curve. The terminal device may extract line segment data of the derivative curve of the signal line segment shown in FIG. 4. Further, some line segments that satisfy a predefined requirement may be captured from the signal line segment shown in FIG. 4 based on a waveform variation feature of the derivative curve. For example, corresponding to an ECG signal, it can be learned based on medical knowledge that in the ECG signal, between a Q wave and an R wave there is a straight line and a turning should not exist. Therefore, if the curve shown in FIG. 4 is a signal line segment used to detect the Q wave and the R wave, only the straight line part on the right of a turning (that is, on the right of a point (60, 0.3)) of the signal line segment shown in FIG. 4 needs to be considered, to be used to detect the Q wave, the R wave, or the like, so that detection accuracy of the waveform signal can be improved.

In this embodiment of this application, the waveform signal may first be marked as a plurality of signal line segments based on the monotonicity, and then the line segment data of the signal line segment may be extracted. Further, after the derivation is performed on the signal line segment, line segment data of a derivative curve of the signal line segment may be extracted, and multi-level extraction may be performed on line segment feature data of the waveform signal. In this embodiment of this application, a feature of each signal line segment that is obtained by marking the waveform signal may be identified by using the multi-level extraction performed on the line segment feature data, to further better identify a waveform feature, identify a period of the waveform signal, and the like. In this way, signal processing quality is higher and a signal period is more accurately identified.

S24. Determine a line segment matching template of the waveform signal based on the line segment data of each signal line segment.

In some feasible implementations, after obtaining, through extraction, the feature data of each of the K signal line segments, including data such as monotonicity of the signal line segment, line segment data of the signal line segment, and line segment data of a derivative curve of the signal line segment, the terminal device may build a line segment matching template of the waveform signal based on the feature data of each signal line segment. For a waveform signal having a period, each period has a similar signal feature (which may be defined as a periodic signal feature). Therefore, in this embodiment of this application, a template for identifying the periodic signal feature may be built, to be used to identify a similar signal feature in each period of the waveform signal. The template for identifying the periodic signal feature may be the line segment matching template provided in this embodiment of this application.

In some feasible implementations, the terminal device may select M target signal line segments whose line segment data is less than a preset line segment data threshold from the line segment data of the signal line segments, and combine the M target signal line segments in a preset line segment combination manner to obtain the line segment matching template of the waveform signal. Specifically, the line segment matching template may include M consecutive signal line segments, that is, signal line segments that are consecutive in time and that are monotonically upward and downward alternately.

Figure 6:
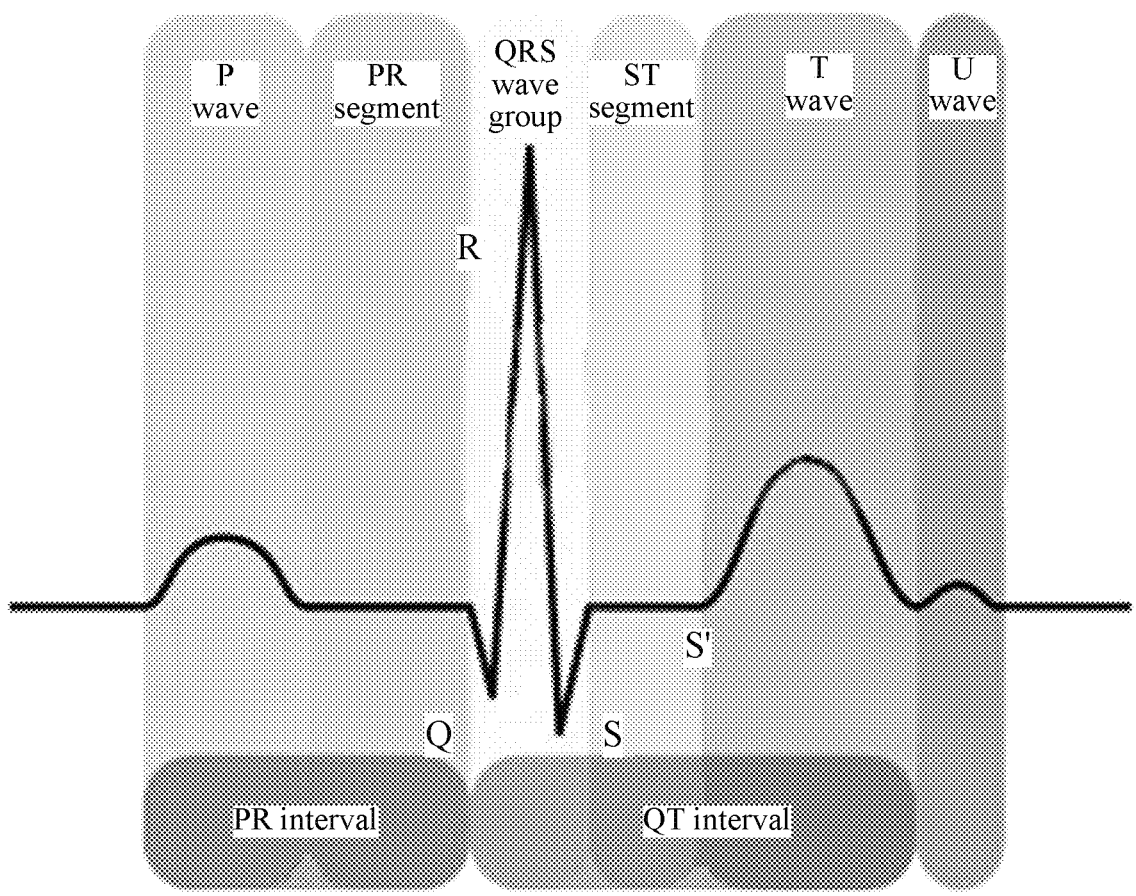
FIG. 6 is a schematic diagram of an ECG signal according to an embodiment of this application.

Optionally, when building a line segment matching template, the terminal device may first select a target signal line segment from the signal line segments of the waveform signal by using preset prior information of the waveform signal. An ECG signal is used as an example. FIG. 6 is a schematic diagram of an ECG signal. Periodic signal data of an ECG signal may include a QRS wave group, a P wave, a T wave, a U wave, a PR segment, an ST segment, and the like. The QRS wave group includes a plurality of signal line segments that are monotonically downward and then monotonically upward and then monotonically downward again. The R point in the QRS wave group is a highest crest in the period, that is, a sharpest waveform crest. A time interval between the R point and the S point is 0.06 second.

Electrocardiograms recorded by different leads are different in waveforms, but a normal electrocardiogram waveform periodogram basically includes a P wave, a QRS wave group, a wave, and a transition period. In addition, a small U wave sometimes appears after the T wave. The characteristic waveforms and transition periods of an electrocardiogram signal are all represent specific physiological significance. Currently, a normal electrocardiogram waveform of an MLH lead is used as an example. As shown in FIG. 6, main compositions of the ECG signal and features thereof are briefly described below.

(1) A P wave is also referred to as an atrial depolarization wave that reflects a potential change in a process of right atrial and left atrial depolarization. The waveform that lasts for 0.08 second to 0.11 second is usually not precipitous and smooth with a wave amplitude that does not exceed 0.25 mV. A potential change generated in a process of the right atrial and left atrial repolarization is referred to as a Ta wave, which is usually overlapped with the PR segment, the QRS wave group, or the ST segment, and a wave amplitude is very low, making it difficult to identify the wave amplitude on the electrocardiogram.

(2) A PR interval (or referred to as a PQ interval) is a time interval between a start point of the P wave and a start point of the QRS wave group and reflects a period of time from the start of the atrial depolarization to the start of ventricle depolarization. A PR interval of a healthy adult is 0.12 second to 0.20 second. If the PR interval exceeds 0.205 second, it usually indicates that atrioventricular block occurs. A time length of the PR interval is related to factors such as age and heart rate. This is not limited herein.

(3) A QRS wave group reflects a potential change in the process of right ventricle and left ventricle depolarization. A typical QRS wave group includes three closely-related potential fluctuations. The first downward wave is referred to as a Q wave followed by an upward and high-sharp R wave and then by a downward S wave. In different leads, the three waves may not all appear, amplitudes of the waves vary greatly, and the waves last for approximately 0.06 second to 0.105 second.

(4) An ST segment refers to a line segment between an end point of the QRS wave group and a start point of the T wave, which is usually flush with a zero potential baseline. In this period, each part of the ventricle is in a depolarization state but the repolarization is not started yet, there is no potential difference between each part of the ventricle, and an electrocardiogram curve recovers to a baseline level. However, when coronary insufficiency, myocardial infarction, or the like occurs, the ST segment usually deviates from the baseline by exceeding a specific amplitude range.

(5) A T wave reflects a potential change in the process of right ventricle and left ventricle repolarization. A waveform of the T wave is not precipitous, a monotonically upward side and a monotonically downward side are not completely symmetrical, a former side of the waveform is relatively long and a latter side is relatively short. A time interval is approximately 0.05 second to 0.255 second. A direction of the T wave needs to be the same as a direction of a main wave of the QRS wave group. In a lead in which the R wave dominates, an amplitude of the T wave needs to be no lower than $\frac{1}{10}$ that of the R wave in the lead.

(6) A QT interval refers to a period of time from the start point of the QRS wave group to an end point of the T wave, and represents time needed from the start of the ventricle depolarization to a complete end of the repolarization. A time length of the interval is closely related to heart rate, and a faster heart rate indicates a shorter QT interval; on the contrary, a slower heart rate indicates a longer QT interval. A normal QT interval may vary due to a difference in a factor such as heart rate, age, or gender. When the heart rate is 75 beats/min, the QT interval is 0.30 second to 0.405 second. Analysis performed on changes of the QT interval can affiliate early diagnosis of diseases and analysis of impact of antiarrhythmic drugs on heart to a particular degree.

(7) A U wave is a U wave with a short width that may appear in 0.02 second to 0.04 second after the T wave and whose direction is the same as that of the T wave.

The periodic signal data may be the prior information of the waveform signal. The terminal device may build a line segment matching template to be used to identify the QRS wave group in the waveform signal. Specifically, the terminal device may use the R point in the QRS wave group as the prior information of the waveform signal such as a highest crest in a period, find a sharpest waveform crest in each preset time interval (for example, 1.5 seconds) of the waveform signal, and sort the obtained waveform crests based on sharpness degrees. Some sharpest crests are deleted, for example, 20% are deleted, and the remaining crests are used to make a line segment matching template. Alternatively, based on the sharpness degrees of the waveform crests, some waveform crests whose sharpness degrees exceed a preset threshold are deleted, and the remaining crests may be used to build a line segment matching template. The features of three lines, namely, the QR line segment, the RS line segment, and a line segment including the point S and a next extreme point may be included in making of a line segment matching template, a median of data of the line segments that meet the related features of the crests is obtained, and the line segment matching template is built by using the obtained median.

Specifically, the terminal device may first search for a small quantity of target signal line segments, builds a template, extracts more target signal line segments by using the template, and updates the template based on the more target signal line segments. A larger quantity of target signal line segments selected by the terminal device indicates higher accuracy of the line segment matching template amended by using line segment data of each signal line segment. Finally, a line segment matching template that is relatively highly similar to the QRS wave group of the waveform signal may be determined.

Optionally, the line segment matching template may be specifically a group of data used as a matching criterion. The group of data includes but is not limited to a length of a line segment, a width of the line segment, coordinate positions of an X axis and a Y axis of a start point of the line segment, a local slope (that is, a local derivative of the signal line segment) near the start point or an end point of the line segment, a slope (for example, in the line segment shown in FIG. 4, a slope of a ray from the start point A (0, 0) to point C (60, 0.3) of the line segment) of a tangential line at which the start point or the end point of the line segment is tangent to the line segment, and the like.

During specific implementation, for a human sign signal such as the ECG signal or a PPG signal, there is a relatively large difference between size signals of individuals, and therefore waveform signals detected by an ECG sensor or a PPG sensor vary in different individuals. In this embodiment of this application, a line segment matching template of a waveform signal may be built based on feature data of each waveform signal, so that processing quality of the waveform signal can be improved and period identification accuracy of the waveform signal can be improved.

S25. Match each of the K signal line segments with M signal line segments included in the line segment matching template, and determine a target wave group of the waveform signal based on a matching result of each signal line segment.

S26. Determine periodic signal data of the waveform signal based on line segment data of the target wave group.

In some feasible implementations, after obtaining the line segment matching template of the waveform signal, the end point may be used to identify a target wave group of the waveform signal in the waveform signal, for example, the QRS wave group in the ECG signal, by using the line segment matching template. Specifically, the terminal device may match each of the K signal line segments obtained by marking the waveform signal with the signal line segments included in the line segment matching template, to search a valid signal line segment in the K signal line segments. The valid signal line segment refers to a signal line segment between Whom and any line segment included in the line segment matching template a matching degree is greater than or equal to a preset similarity threshold. To be specific, the valid signal line segment is a line segment between Whom and any line segment included in the line segment matching template a feature difference is less than a preset threshold. Further, signal features of wave groups including N valid signal line segments obtained through searching may be matched with signal features of a wave group including the signal line segments included in the line segment matching template. If a feature difference between the signal features of the wave groups is less than the preset threshold, it may be determined that a wave group that is similar to the line segment matching template and that is in the wave group including the N valid signal is the target wave group. For example, if a wave group including three signal line segments in the N valid signal line segment j is similar to the QRS wave group including the line segment matching template, it may be determined that the wave group including the three valid signal line segment j is the target wave group, that is, the QRS wave group.

For example, after being filtered, an ECG signal having a time length of one minute may be marked as approximately 1500 signal line segments. Specifically, a quantity of the signal line segment j is related to filtering strength of a waveform signal and may be specifically determined based on an actual application scenario. This is merely described by way of example herein. The line segment matching template includes three signal line segments (target signal line segments), for example, signal line segments QR, RS, and SS' (where a monotonically upward line segment after the S point may be marked as SS', as shown in FIG. 6). Each of the 1500 signal line segments that is to be checked is matched with the three target signal line segments, that is, 4500 times of matching are to be performed. Specifically, during each execution, using QR as an example, it is assumed that a length of the target signal line segment QR is QR.L. If a line segment width of a to-be-checked signal line segment falls within a width range of 50% to 200% of QR.L, it may be determined through detection that the width of the signal line segment is qualified. Then, similarly, a length of the signal line segment is detected, and parameters such as a local slope near a start point or an end point of the signal line segment, a slope of a ray from the start point or the end point of the signal line segment to the line segment are detected. If each parameter is successfully matched, the valid signal line segment may be determined. Further, a feature of a wave group including a plurality of consecutive signal line segments in the valid signal line segment may be detected, so that the target wave group may further be determined. During the matching of the valid signal line segment, the valid signal line segment further includes a signal line segment on the right of the turning in addition to a line segment on the left of the turning. That is, the signal line segment that includes the turning does not conform to a feature of the line segment QR. The turning may be formed due to an error during data collection, or due to another environmental factor, or the like. If in a matching result of the valid signal line segment, three valid signal line segments whose time sequence numbers are consecutive respectively match QR, RS, and SS' in the line segment matching template successfully, it may be determined that a wave group including the three valid signal line segments is a QRS wave group, that is, the target wave group.

Optionally, after identifying the target wave group, the terminal device may identify a period of the waveform signal based on the target wave group. The terminal device may further determine a period of the waveform signal based on the neighboring waveform signal of the target wave group and preset period checking data. The neighboring waveform signal of the target wave group may include line segment data of a plurality of neighboring signal line segments of the valid signal line segment of the target wave group. The neighboring waveform signal may present a crest or trough other than the target wave group, for example, a wave, a U wave, or a P wave in an ECG. The period checking data includes a waveform width of the period, a waveform amplitude of the period, a waveform height of a start point of the period, and a waveform height of an end point of the period, and the like. This is not limited herein.

For example, there is only one wave in the ECG signal, and the P wave is not higher than the R wave or is even much lower than the R wave. The waveform after the S point should not continue to be drastically downward. For another example, a waveform amplitude of PPG and heights of a start point and an end point of a period are limited. These may all be referred to as period checking data or checking data of the neighboring waveform signal of the target wave group.

For example, the T wave in the ECG signal is a protrusion in a period of time after the QRS wave group. Usually, a crest in a T wave in an ECG signal of an individual whose heart is not healthy is relatively high. If the wave in the ECG signal is inverted, it indicates that the individual has a sign such as angina pectoris. Therefore, detection quality of the waveform signal can be controlled and period identification accuracy can be improved by detecting whether there is a T wave after the QRS wave group and a width of the T wave and whether a height is proper.

Optionally, after identifying the target wave group or periodic signal data of the waveform signal, the terminal device may delete, based on the identified information, a waveform signal having an abnormal period in the waveform signals, or repair the waveform signal having the abnormal period. For example, after the terminal device identifies the target wave group, a heart rate period may be found. For example, if a period in the waveform signal is missing, identified heartbeat intervals may be one second, one second, one second, two seconds, one second, and the like. Therefore, it may be determined that a waveform period is missing in the middle. In this case, the waveform signal in the period may fail to pass the periodic signal data matching. The terminal device may lower a data threshold criterion such as a preset period threshold of period checking data to re-match the waveform signal, to save a period through period identification. On the contrary, if the heart intervals are one second, one second, 0.3 second, 0.7 second, and one second, it may be determined that there is an excessive period in the identified heartbeat periods. In this case, noise may be identified as a heart rate period, and an operation such as performing identification on the waveform signal again may further be performed to delete the noise.

Optionally, if the identified periodic signal data of the waveform signal is an isolated period and neighboring signals of the period are noise, the period may also be noise, and signal data of the period is not applicable and therefore may be discarded.

The terminal device may identify each period in the waveform signal based on the determined periodic signal data of the waveform signal, and may further determine feature data of periods to delete a signal having an abnormal period in the waveform signal, thereby improving detection accuracy of the waveform signal.

Figure 7:
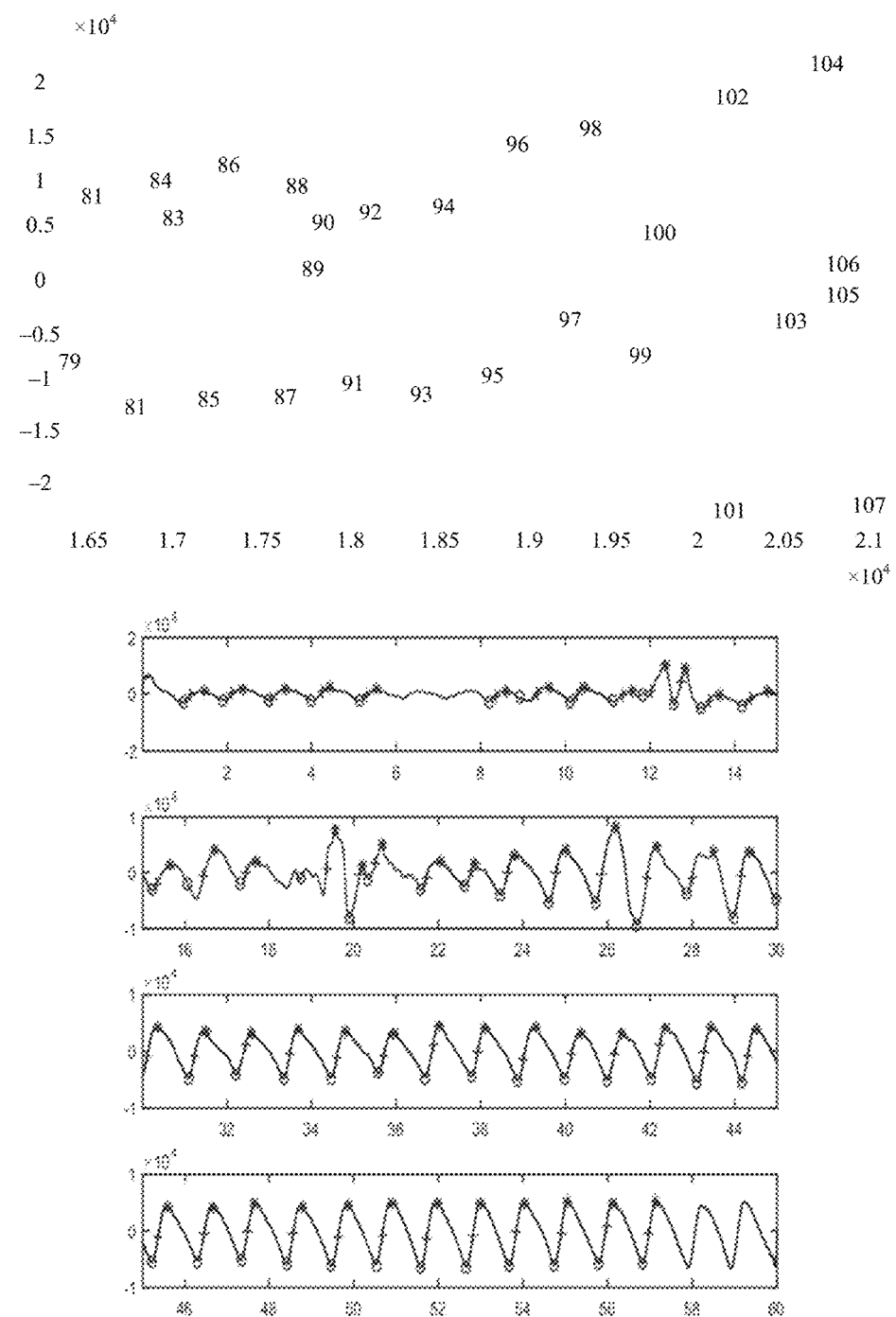
FIG. 7 is a schematic diagram of a PPG signal according to an embodiment of this application.

FIG. 7 is a schematic diagram of a PPG signal according to an embodiment of this application. FIG. 7 shows a PPG waveform. The terminal device may identify periodic signal data of a single period of a PPG signal based on the implementations described in the foregoing steps, or may identify a waveform similarity between periods, to further delete a signal having an abnormal period in the waveform signal.

Figure 8:
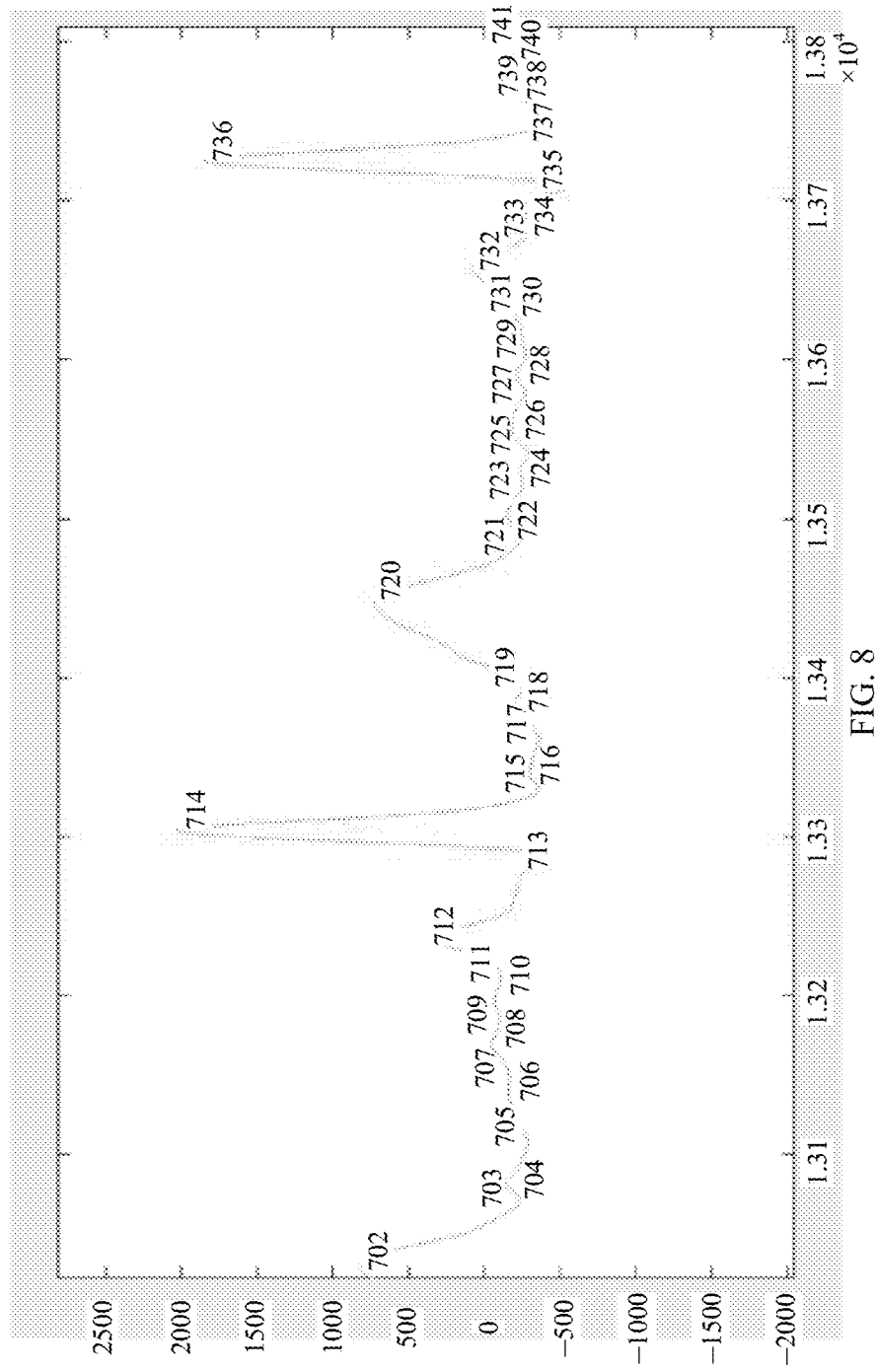
FIG. 8 is a schematic diagram of an ECG waveform signal according to an embodiment of this application.

FIG. 8 is a schematic diagram of an ECG waveform signal according to an embodiment of this application. FIG. 8 shows an ECG waveform. The terminal device may identify data of a waveform signal of each period based on the implementations described in the foregoing steps. A feature of a waveform signal (or prior information of the waveform signal) of an ECG may include P, Q, R, S, and T points, where a peak of a P wave is marked with 712, the Q, R, and S points are marked with 713, 714, and 715, and a peak of a T wave is marked with 720.

In this embodiment of this application, the line segment data of a signal line segment may be extracted from the waveform signal, processing such as derivation may further be performed on the signal line segment and line segment data of a derivative curve may be extracted, and a line segment matching template that is used for identifying the periodic signal data of the waveform signal may be built based on the extracted data. Further, a period of the waveform signal may be identified by using the line segment matching template, and noise is deleted. The line segment matching template provided in this embodiment of this application may be built based on the line segment data of the waveform signal. The line segment matching template may vary due to different feature data of the waveform signal, so that association between the line segment matching template and the line segment data of the waveform signal can be improved, period identification accuracy of the waveform signal can be improved, and noise deletion accuracy is improved, thereby improving processing quality of the waveform signal.

Figure 9:
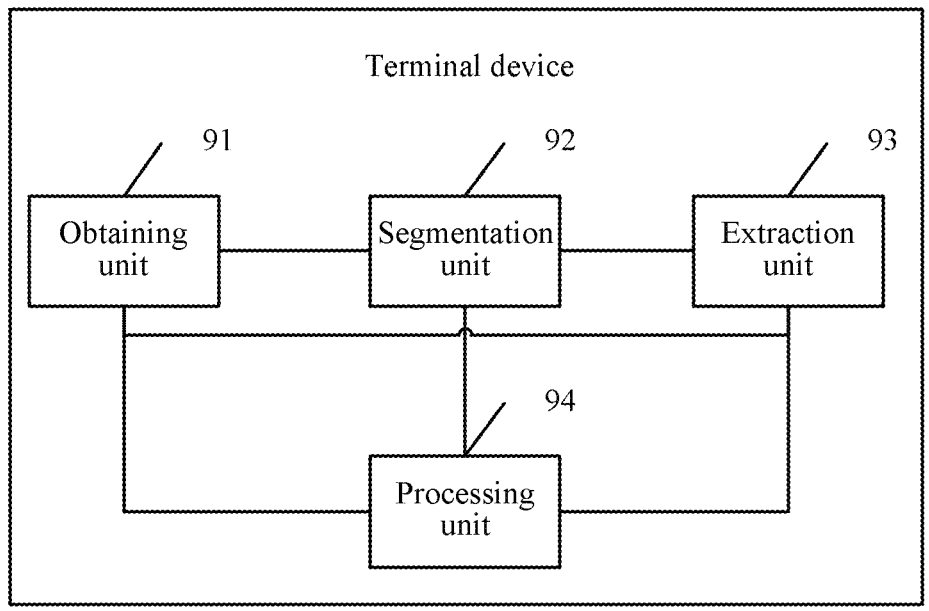
FIG. 9 is a schematic structural diagram of a waveform signal processing apparatus according to an embodiment of this application.

FIG. 9 is a schematic structural diagram of a waveform signal processing apparatus according to an embodiment of this application. The waveform signal processing apparatus provided in this embodiment of this application may be specifically the terminal device provided in the embodiments of this application. The terminal device may include:

an obtaining unit 91, configured to obtain a filtered waveform signal;

a segmentation unit 92, configured to mark the waveform signal obtained by the obtaining unit as K signal line segments based on monotonicity, where K is an integer greater than or equal to 2;

an extraction unit 93, configured to extract line segment data of each signal line segment obtained by the segmentation unit through processing; and a processing unit 94, configured to determine a line segment matching template of the waveform signal based on line segment data of each signal line segment extracted by the extraction unit, where the line segment matching template includes M consecutive signal line segments, and M is an integer less than K.

the processing unit 94 is further configured to: match each of the K signal line segments obtained by the segmentation unit through processing with the M signal line segments included in the line segment matching template, and determine a target wave group of the waveform signal based on a matching result of each signal line segment; and the processing unit 94 is further configured to determine, based on line segment data of the target wave group, periodic signal data of the waveform signal obtained by the obtaining unit.

Optionally, the segmentation unit 92 is configured to:

divide the waveform signal into monotonically upward signal line segments or monotonically downward signal line segments based on the monotonicity, and sequentially number the signal line segments based on time continuity to obtain line segments having sequential numbers.

Optionally, the extraction unit 93 is configured to:

extract a line segment length Xi and a line segment width Yi of the signal line segment and perform difference extension on Xi and Yi based on a preset length and a preset width respectively to obtain a normalized signal line segment j; and extract line segment data of the signal line segment j, where the line segment data of the signal line segment j includes at least one of: a middle point position of the line segment, a curvature of a start point position of the line segment, a curvature of an end point position of the line segment, a ray tangent point at which the start point position of the line segment is tangent to the line segment, and a ray tangent point at which the end point position of the line segment is tangent to the line segment.

Optionally, the extraction unit 93 is further configured to:

derive or differentiate the signal line segment j to obtain a derivative curve of the signal line segment j, and extract line segment data of the derivative curve, where the line segment data of the derivative curve includes at least one of: a quantity of inflection points, positions of the inflection points, a middle point position between neighboring inflection points, and a position of an inflection point at which a crest value is the largest.

Optionally, the processing unit 94 is configured to:

select M target signal line segments whose line segment data is less than a preset line segment data threshold from the line segment data of the signal line segments, and combine the M target signal line segments in a preset line segment combination manner to obtain the line segment matching template of the waveform signal, where the M target signal line segments are line segments whose sequence numbers are consecutive.

Optionally, the processing unit 94 is configured to:

match the line segment data of each of the K signal line segments with the line segment data of each of the NI target signal line segments included in the line segment matching template, and determine N valid signal line segments in the K signal line segments, where N is an integer less than M, and a feature difference between line segment data of the valid signal line segment and line segment data of any target line segment included in the line segment matching template is not less than a preset threshold; and if the N valid signal line segments include M valid signal line segments whose sequence numbers are consecutive, and a feature difference between each of the M valid signal line segments and the M target signal line segments included in the line segment matching template is less than the preset threshold, determine that positions of the M valid signal line segments are positions of a target wave group.

Optionally, line segment data at the positions of the target wave group includes the line segment data of the M valid signal line segments at the positions of the target wave group and line segment data of J neighboring signal line segments whose sequence numbers are consecutive to the sequence numbers of the M valid signal line segments.

The processing unit 94 is configured to:

determine, based on the line segment data of the M valid signal line segments and the line segment data of the J neighboring signal line segments, at least one type of the following wave group feature data: a waveform width of a wave group including the M valid signal line segments and the J neighboring signal line segments, a waveform amplitude of the wave group, a height of a start point of the wave group, or fluctuation of an end point of the wave group; and if a feature difference between the wave group feature data and period checking data is less than a preset period threshold, determine that the wave group is a period of the waveform signal and the wave group feature data of the wave group is the periodic signal data of the waveform signal, where the period checking data includes at least one of: a waveform width of the period, a waveform amplitude of the period, a waveform height of a start point of the period, and a waveform height of an end point of the period.

Optionally, the processing unit 94 is further configured to:

determine, based on the periodic signal data of the waveform signal, a plurality of waveform periods included in the waveform signal, and delete abnormal period data included in the waveform signal, where the abnormal period data is line segment data of a wave group that does not include the periodic signal data in the waveform signal.

Optionally, the waveform signal includes at least one of: an electrocardiogram ECG, a photoplethysmogram PPG, a pressure gauge signal, a magnetometer signal, and an accelerometer sensor waveform signal.

During specific implementation, the terminal device may perform, by using built-in units in the terminal device, the implementations performed by the terminal device in the foregoing embodiments. For details, refer to the implementations described in the steps of the foregoing embodiments. This is not described herein again.

In this embodiment of this application, the terminal device may extract line segment data of a signal line segment from the waveform signal, processing such as derivation may further be performed on the signal line segment and line segment data of a derivative curve may be extracted, and a line segment matching template that is used for identifying the periodic signal data of the waveform signal may be built based on the extracted data. Further, a period of the waveform signal may be identified by using the line segment matching template, and noise is deleted. The line segment matching template provided in this embodiment of this application may be built based on the line segment data of the waveform signal. The line segment matching template may vary due to different feature data of the waveform signal, so that association between the line segment matching template and the line segment data of the waveform signal can be improved, period identification accuracy of the waveform signal can be improved, and noise deletion accuracy is improved, thereby improving processing quality of the waveform signal.

Figure 10:
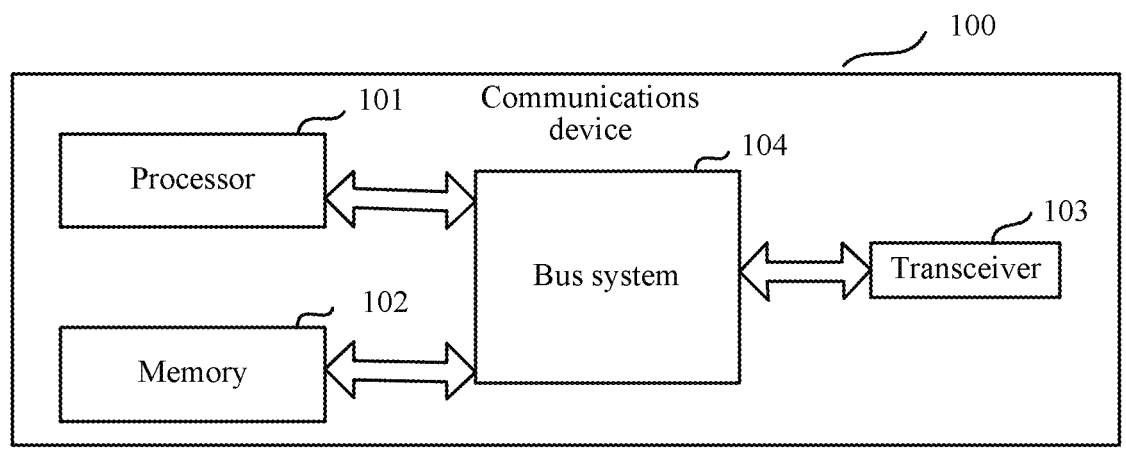
FIG. 10 is a schematic structural diagram of a communications device according to an embodiment of this application.

FIG. 10 is a schematic structural diagram of a communications device according to an embodiment of this application. As shown in FIG. 10, the communications device 100 provided in this embodiment of this application includes a processor 101, a memory 102, a transceiver 103, and a bus system 104.

The processor 101, the memory 102, and the transceiver 103 are connected by using the bus system 104.

The memory 102 is configured to store a program. Specifically, the program may include program code, where the program code includes a computer operation instruction. The memory 102 includes but is not limited to a (random access memory (random access memory, RAM), a read-only memory (read-only memory, ROM), an erasable programmable read-only memory (erasable programmable read-only memory, EPROM), or a compact disc read-only memory (compact disc read-only memory, CD-ROM). FIG. 10 shows only one memory. Certainly, it may be set that there are a plurality of memories based on needs. The memory 102 may alternatively be the memory in the processor 101. This is not limited herein.

The memory 102 stores the following elements, executable modules or data structures, or a subset thereof, or an extension set thereof:

operation instructions, including various operation instructions and used to perform various operations; and an operating system, including various system programs and configured to implement various basic services and process a hardware-based task.

The processor 101 controls an operation of the communications device 100, and the processor 101 may be one or more central processing units (central processing unit, CPU). When the processor 101 is a CPU, the CPU may be a single-core CPU or may be a multi-core CPU.

During specific application, components of the communications device 100 are coupled together by using a bus system 104, where in addition to a data bus, the bus system 104 may include a power bus, a control bus, a status signal bus, and the like. However, for clear description, various types of buses in FIG. 10 are marked as the bus system 104. For ease of illustration, the bus system 104 is merely schematically drawn in FIG. 10.

The method that is of the terminal device and that is disclosed in the foregoing embodiments may be applied to the processor 101, or in other words, may be implemented by the processor 101. The processor 101 may be an integrated circuit chip and has a signal processing capability. In an implementation process, steps in the foregoing methods can be implemented by using a hardware integrated logical circuit in the processor 101, or by using instructions in a form of software. The processor 101 may be a general-purpose processor, a digital signal processor (digital signal processing, DSP), an application-specific integrated circuit (application specific integrated circuit, ASIC), a field-programmable gate array (field-programmable gate array, FPGA) or another programmable logic device, a discrete gate or a transistor logic device, or a discrete hardware component. It may implement or perform the methods, the steps, and logical block diagrams that are disclosed in the embodiments of this application. The general-purpose processor may be a microprocessor, or the processor may be any conventional processor or the like. Steps of the methods disclosed with reference to the embodiments of this application may be directly executed and accomplished by using a hardware decoding processor, or may be executed and accomplished by using a combination of hardware and software modules in the decoding processor. A software module may be located in a mature storage medium in the art, such as a random access memory, a flash memory, a read-only memory, a programmable read-only memory, an electrically erasable programmable memory, a register, or the like. The storage medium is located in the memory 102. The processor 101 reads information in the memory 102 and performs, in combination with hardware of the processor, the steps of the foregoing methods of the terminal device described in the embodiments.

A person of ordinary skill in the art may understand that all or a part of the processes of the methods in the embodiments may be implemented by a computer program instructing relevant hardware. The program may be stored in a computer-readable storage medium. When the program runs, the processes of the methods in the embodiments are performed. The storage medium may be a magnetic disk, an optical disk, a ROM/RAM, and the like.

What is claimed is:

1. An electrocardiogram waveform signal processing method implemented by a terminal, wherein the terminal comprises a sensor and a processor, and wherein the electrocardiogram waveform signal processing method comprises:
    obtaining, by the sensor, a filtered electrocardiogram waveform signal;
    marking, by the processor, the filtered electrocardiogram waveform signal as K signal line segments based on monotonicity, wherein K is an integer greater than or equal to two, and wherein marking the filtered electrocardiogram waveform signal comprises:
        dividing the filtered electrocardiogram waveform signal into monotonically upward signal line segments or monotonically downward signal line segments based on monotonicity; and
        sequentially numbering the K signal line segments based on time continuity to obtain line segments having sequential numbers;
    extracting, by the processor, first line segment data of each of the K signal line segments by:
        extracting, by the processor, a line segment length Xi and a line segment width Yi of each signal line segment i of the K signal line segments;
        performing difference extension on the line segment length Xi and the line segment width Yi based on a preset length and a preset width, respectively, to obtain a normalized signal line segment j; and
        extracting, by the processor, fourth line segment data of the normalized signal line segment j, wherein the fourth line segment data of the normalized signal line segment j comprises at least one of a middle point position of the normalized signal line segment j, a curvature of a start point position of the normalized signal line segment j, a curvature of an end point position of the normalized signal line segment j, a ray tangent point at which the start point position of the normalized signal line segment j is tangent to the normalized signal line segment j, and a ray tangent point at which the end point position of the normalized signal line segment j is tangent to the normalized signal line segment j;
    generating a line segment matching template of the filtered electrocardiogram waveform signal based on the first line segment data, wherein the line segment matching template comprises M consecutive signal line segments, and wherein M is an integer less than K;
    matching, by the processor, each of the K signal line segments with the M consecutive signal line segments;
    determining a target wave group of the filtered electrocardiogram waveform signal based on a matching result of each of the K signal line segments; and
    determining, by the processor, periodic signal data of the filtered electrocardiogram waveform signal based on second line segment data of the target wave group.

2. The electrocardiogram waveform signal processing method of claim 1, further comprising:
    differentiating, by the processor, the normalized signal line segment j to obtain a derivative curve of the normalized signal line segment j; and
    extracting fifth line segment data of the derivative curve, wherein the fifth line segment data of the derivative curve comprises at least one of a quantity of inflection points, positions of the inflection points, a middle point position between neighboring inflection points, or a position of an inflection point at which a crest value is largest.

3. The electrocardiogram waveform signal processing method of claim 1, wherein determining the line segment matching template of the filtered electrocardiogram waveform signal comprises:
    selecting M target signal line segments whose sixth line segment data is less than a preset line segment data threshold from the first line segment data of the K signal line segments; and
    combining the M target signal line segments in a preset line segment combination manner to obtain the line segment matching template of the filtered electrocardiogram waveform signal, wherein the M target signal line segments have consecutive sequence numbers.

4. The electrocardiogram waveform signal processing method of claim 3, wherein matching each of the K signal line segments with the M consecutive signal line comprises:
    matching, by the processor, the first line segment data of each of the K signal line segments with the sixth line segment data of each of the M target signal line segments comprised in the line segment matching template;
    determining N valid signal line segments of the K signal line segments, wherein N is an integer less than M, and wherein a feature difference between seventh line segment data of each valid signal line segment of the N valid line segments and the sixth line segment data is not less than a preset threshold; and
    determining that positions of M valid signal line segments whose sequence numbers are consecutive are positions of a target wave group when the N valid signal line segments comprise the M valid signal line segments, and a feature difference between each of the M valid signal line segments and the M target signal line segments comprised in the template is less than the preset threshold.

5. The electrocardiogram waveform signal processing method of claim 4, wherein eighth line segment data at the positions of the target wave group comprises ninth line segment data of the M valid signal line segments at the positions of the target wave group and tenth line segment data of J neighboring signal line segments whose sequence numbers are consecutive to the sequence numbers of the M valid signal line segments, and wherein the determining the periodic signal data of the filtered electrocardiogram waveform signal comprises:
    determining, by the processor, based on the ninth line segment data of the M valid signal line segments and the tenth line segment data of the J neighboring signal line segments, at least one type of wave group feature data comprising an electrocardiogram waveform width of a wave group consisting of the M valid signal line segments and the J neighboring signal line segments, an electrocardiogram waveform amplitude of the wave group, a height of a start point of the wave group, or fluctuation of an end point of the wave group; and
    determining that the wave group is a period of the filtered electrocardiogram waveform signal and the wave group feature data is the periodic signal data of the filtered electrocardiogram waveform signal when a feature difference between the wave group feature data and period checking data is less than a preset period threshold, wherein the period checking data comprises at least one of a waveform width of the period, a waveform amplitude of the period, a waveform height of a start point of the period, or a waveform height of an end point of the period.

6. The electrocardiogram waveform signal processing method of claim 5, wherein the electrocardiogram waveform signal processing method further comprises:
 determining, by the processor, based on the periodic signal data of the filtered electrocardiogram waveform signal, waveform periods comprised in the filtered electrocardiogram waveform signal; and
 deleting abnormal period data comprised in the filtered electrocardiogram waveform signal, wherein the abnormal period data is line segment data of a wave group that does not comprise the periodic signal data in the filtered electrocardiogram waveform signal.

7. The electrocardiogram waveform signal processing method of claim 1, wherein the sensor comprises an electrocardiogram sensor.

8. The electrocardiogram waveform signal processing method of claim 1, wherein the terminal comprises a wearable device.

9. An electrocardiogram waveform signal processing apparatus, comprising:
 a processor; and
 a memory coupled to the processor and storing one or more programs that, when executed by the processor, cause the electrocardiogram waveform signal processing apparatus to be configured to:
  obtain a filtered electrocardiogram waveform signal;
  mark the filtered electrocardiogram waveform signal as K signal line segments based on monotonicity, wherein K is an integer greater than or equal to two, and wherein the marking is further configured to:
   divide the filtered electrocardiogram waveform signal into monotonically upward signal line segments or monotonically downward signal line segments based on monotonicity; and
   sequentially number the signal line segments based on time continuity to obtain line segments having sequential numbers;
  extract first line segment data of each of the K signal line segments by:
   extracting a line segment length Xi and a line segment width Yi of each signal line segment i of the K signal line segments;
   performing difference extension on the line segment length Xi and the line segment width Yi based on a preset length and a preset width, respectively, to obtain a normalized signal line segment j; and
   extracting third line segment data of the normalized signal line segment j, wherein the third line segment data of the normalized signal line segment j comprises at least one of a middle point position of the normalized signal line segment j, a curvature of a start point position of the normalized signal line segment j, a curvature of an end point position of the normalized signal line segment j, a ray tangent point at which the start point position of the normalized signal line segment j is tangent to the normalized signal line segment j, and a ray tangent point at which the end point position of the normalized signal line segment j is tangent to the normalized signal line segment j;
  determine a line segment matching template of the filtered electrocardiogram waveform signal based on the first line segment data, wherein the line segment matching template comprises M consecutive signal line segments, and wherein M is an integer less than K;
  match each of the K signal line segments with the M consecutive signal line segments;
  determine a target wave group of the filtered electrocardiogram waveform signal based on a matching result of each of the K signal line segments; and
  determine, based on second line segment data of the target wave group, periodic signal data of the filtered electrocardiogram waveform signal.

10. The electrocardiogram waveform signal processing apparatus of claim 9, wherein the one or more programs are further configured to cause the electrocardiogram waveform signal processing apparatus to:
 differentiate the normalized signal line segment j to obtain a derivative curve of the normalized signal line segment j; and
 extract fourth line segment data of the derivative curve, wherein the fourth line segment data of the derivative curve comprises at least one of a quantity of inflection points, positions of the inflection points, a middle point position between neighboring inflection points, or a position of an inflection point at which a crest value is largest.

11. The electrocardiogram waveform signal processing apparatus of claim 9, wherein the one or more programs are further configured to cause the electrocardiogram waveform signal processing apparatus to:
 select M target signal line segments whose fourth line segment data is less than a preset line segment data threshold from the first line segment data of the K signal line segments, wherein the M target signal line segments have consecutive sequence numbers; and
 combine the M target signal line segments in a preset line segment combination manner to obtain the line segment matching template of the filtered electrocardiogram waveform signal.

12. The electrocardiogram waveform signal processing apparatus of claim 11, wherein the one or more programs are further configured to cause the electrocardiogram waveform signal processing apparatus to:
 match the first line segment data of each of the K signal line segments with the fourth line segment data of each of the M target signal line segments;
 determine N valid signal line segments of the K signal line segments, wherein N is an integer less than M, and wherein a feature difference between fifth line segment data of each of the N valid signal line segments and the fourth line segment data is not less than a preset threshold; and
 determine that positions of M valid signal line segments whose sequence numbers are consecutive are positions of a target wave group when the N valid signal line segments comprise the M valid signal line segments and a feature difference between each of the N valid signal line segments and the M target signal line segments is less than the preset threshold.

13. The electrocardiogram waveform signal processing apparatus of claim 12, wherein sixth line segment data at the positions of the target wave group comprises seventh line segment data of the M valid signal line segments at the positions of the target wave group and eighth line segment data of J neighboring signal line segments whose sequence numbers are consecutive to the sequence numbers of the M valid signal line segments, and wherein the one or more programs are further configured to cause the electrocardiogram waveform signal processing apparatus to:
 determine, based on the seventh line segment data and the eighth line segment data, at least one type of wave group feature data comprising a waveform width of a wave group including the M valid signal line segments and the J neighboring signal line segments, a waveform amplitude of the wave group, a height of a start point of the wave group, or a fluctuation of an end point of the wave group; and determine that the wave group is a period of the filtered electrocardiogram waveform signal and the wave group feature data is the periodic signal data of the filtered electrocardiogram waveform signal when a feature difference between the wave group feature data and period checking data is less than a preset period threshold, wherein the period checking data comprises at least one of a waveform width of the period, a waveform amplitude of the period, a waveform height of a start point of the period, or a waveform height of an end point of the period.

14. The electrocardiogram waveform signal processing apparatus of claim 13, wherein the one or more programs are further configured to cause the electrocardiogram waveform signal processing apparatus to:

determine electrocardiogram waveform periods comprised in the filtered electrocardiogram waveform signal based on the periodic signal data of the filtered electrocardiogram waveform signal; and delete abnormal period data comprised in the filtered electrocardiogram waveform signal, wherein the abnormal period data is line segment data of a wave group that does not comprise the periodic signal data in the filtered electrocardiogram waveform signal.

15. The electrocardiogram waveform signal processing apparatus of claim 9, further comprising an electrocardiogram sensor configured to obtain the filtered electrocardiogram waveform signal.

16. The electrocardiogram waveform signal processing apparatus of claim 9, wherein the electrocardiogram waveform signal processing apparatus further comprises a wearable device.

17. A computer program product comprising computer-executable instructions stored on a non-transitory computer-readable medium that, when executed by a processor, cause an apparatus to:

obtain, from a sensor, a filtered electrocardiogram waveform signal;

mark the filtered electrocardiogram waveform signal as K signal line segments based on monotonicity, wherein K is an integer greater than or equal to two, and wherein the apparatus is configured to mark the filtered electrocardiogram waveform signal as the K signal line segments by:

dividing the filtered electrocardiogram waveform signal into monotonically upward signal line segments or monotonically downward signal line segments based on monotonicity; and sequentially numbering the signal line segments based on time continuity to obtain line segments having sequential numbers;

extract first line segment data of each of the K signal line segments by:

extracting a line segment length Xi and a line segment width Yi of each signal line segment i of the K signal line segments;

performing difference extension on the line segment length Xi and the line segment width Yi based on a preset length and a preset width respectively to obtain a normalized signal line segment j; and extracting third line segment data of the normalized signal line segment j, wherein the third line segment data of the normalized signal line segment j comprises at least one of a middle point position of the normalized signal line segment j, a curvature of a start point position of the normalized signal line segment j, or a curvature of an end point position of the normalized signal line segment j;

determine a line segment matching template of the filtered electrocardiogram waveform signal based on the first line segment data, wherein the line segment matching template comprises M consecutive signal line segments, and wherein M is an integer less than K;

match each of the K signal line segments with the M consecutive signal line segments;

determine a target wave group of the filtered electrocardiogram waveform signal based on a matching result of each of the K signal line segments; and determine, based on second line segment data of the target wave group, periodic signal data of the filtered electrocardiogram waveform signal.

18. The computer program product of claim 17, wherein the computer-executable instructions further cause the apparatus to:

differentiate the normalized signal line segment j to obtain a derivative curve of the normalized signal line segment j; and extract fourth line segment data of the derivative curve, wherein the fourth line segment data of the derivative curve comprises at least one of a quantity of inflection points, positions of the inflection points, a middle point position between neighboring inflection points, or a position of an inflection point at which a crest value is largest.

19. The computer program product of claim 17, wherein the computer-executable instructions further cause the apparatus to:

select M target signal line segments whose fourth line segment data is less than a preset line segment data threshold from the first line segment data of the K signal line segments, wherein the M target signal line segments have consecutive sequence numbers; and combine the M target signal line segments in a preset line segment combination manner to obtain the line segment matching template of the filtered electrocardiogram waveform signal.

20. The computer program product of claim 17, wherein the sensor comprises an electrocardiogram sensor, and wherein the apparatus comprises a wearable device.

* * * * *